US011145181B1

United States Patent
Lee et al.

(10) Patent No.: US 11,145,181 B1
(45) Date of Patent: Oct. 12, 2021

(54) METHOD AND WEARABLE ELECTRONIC DEVICE FOR IMBALANCE WARNING

(71) Applicant: National Tsing Hua University, Hsinchu (TW)

(72) Inventors: Yun-Ju Lee, Hsinchu (TW); Yu-Tang Wen, Toufen (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 17/031,121

(22) Filed: Sep. 24, 2020

(30) Foreign Application Priority Data

May 26, 2020 (TW) ................................ 10911745.8

(51) Int. Cl.
*G08B 31/00* (2006.01)
*G08B 21/18* (2006.01)
*G08B 7/06* (2006.01)
*G01P 15/18* (2013.01)
*A61B 5/11* (2006.01)
*A61B 5/00* (2006.01)
*G06F 3/16* (2006.01)

(52) U.S. Cl.
CPC .......... *G08B 21/182* (2013.01); *A61B 5/1117* (2013.01); *A61B 5/4023* (2013.01); *A61B 5/6803* (2013.01); *G01P 15/18* (2013.01); *G08B 7/06* (2013.01); *A61B 2562/0219* (2013.01); *G06F 3/165* (2013.01)

(58) Field of Classification Search
CPC ......... G08B 21/182; G08B 7/06; G01P 15/18; G06F 3/165; A61B 5/4023; A61B 2562/0219; A61B 5/1117; A61B 5/6803
See application file for complete search history.

(56) References Cited

U.S. PATENT DOCUMENTS

| 2008/0133171 A1* | 6/2008 | Feichtinger .......... G01C 22/006 702/141 |
| 2017/0148297 A1* | 5/2017 | Ross .................... G08B 21/043 |
| 2018/0000385 A1* | 1/2018 | Heaton ................ G08B 29/186 |
| 2018/0279915 A1 | 10/2018 | Huang et al. |

(Continued)

FOREIGN PATENT DOCUMENTS

| CN | 103976739 A | 8/2014 |
| CN | 108652637 A | 10/2018 |
| CN | 110279420 A | 9/2019 |

(Continued)

OTHER PUBLICATIONS

Taiwanese Search Report for Taiwanese Application No. 109117458, dated Feb. 20, 2021, with an English translation.

*Primary Examiner* — Hongmin Fan
(74) *Attorney, Agent, or Firm* — Birch, Stewart, Kolasch & Birch, LLP (57) ABSTRACT

A method for imbalance warning to be implemented by a wearable electronic device positioned on a body part of a user includes steps of: obtaining acceleration data during a calibration period; obtaining an angle threshold based on the acceleration data thus obtained; obtaining angular velocity data during a unit of time; calculating a sway angle based on the angular velocity data; determining whether the sway angle thus calculated exceeds the angle threshold; and when it is determined that the sway angle exceeds the angle threshold, outputting a signal that indicates imbalance of the user.

13 Claims, 9 Drawing Sheets

(56) References Cited

U.S. PATENT DOCUMENTS

2019/0114895 A1* 4/2019 Tang .................. G06T 7/12
2020/0111345 A1* 4/2020 Li .................. H04B 1/385

FOREIGN PATENT DOCUMENTS

| TW | 201443834 A | 11/2014 |
| TW | I556198 B | 11/2016 |
| TW | 201822742 A | 7/2018 |
| TW | I668674 B | 8/2019 |
| WO | WO 2019/086997 A2 | 5/2019 |

* cited by examiner

METHOD AND WEARABLE ELECTRONIC DEVICE FOR IMBALANCE WARNING

CROSS-REFERENCE TO RELATED APPLICATION

This application claims priority of Taiwanese Invention Patent Application No. 109117458, filed on May 26, 2020.

FIELD

The disclosure relates to a method and a wearable electronic device for imbalance warning, and more particularly to a method and a wearable electronic device for imbalance warning based on gait analysis.

BACKGROUND

Postural balance of a human body is achieved and maintained by a sensorimotor control system, in which the neural controller uses feedback information from sensory modalities (visual, proprioceptive, vestibular, auditory, etc.) to actuate the musculoskeletal system in order to execute intended movements. Factors such as injury, disease, drug and aging may cause postural imbalance, which may further cause falls, which often result in serious consequences in the elderly.

A conventional assistive device for balance-maintaining or rehabilitation is designed generally based on normal (i.e., balanced) gait patterns of ordinary and healthy people, in the hope that muscles of a user of such device may be trained so that the user may regain normal sense of balance and achieve a normal gait pattern after using the device for a certain period of time. However, due to lack of consideration of personal balance control ability that relates to physical and psychological factors of each user, said device may be unsuitable to certain (e.g., elder) users.

SUMMARY

Therefore, an object of the disclosure is to provide methods and a wearable electronic device for imbalance warning that can alleviate at least one of the drawbacks of the prior art. The methods for imbalance warning are to be implemented by the wearable electronic device that is positioned on a body part of a user. The wearable electronic device includes an inertial measurement unit (IMU), an output unit and a processing unit that is electrically connected to the IMU and the output unit.

A method in accordance with an aspect of the disclosure includes steps of: by the IMU, obtaining acceleration data related to the wearable electronic device during a calibration period, in which the user continuously takes a plurality of steps walking on the ground while maintaining balance; by the processing unit, obtaining an angle threshold based on the acceleration data thus obtained, the angle threshold being associated with the user and being related to sway of the body part of the user; by the IMU, obtaining angular velocity data of the wearable electronic device during a unit of time; by the processing unit, calculating a sway angle of the body part with respect to the unit of time based on the angular velocity data measured during the unit of time; by the processing unit, determining whether the sway angle thus calculated exceeds the angle threshold; and by the processing unit, when it is determined that the sway angle exceeds the angle threshold, controlling the output unit to output a first signal that indicates imbalance of the user.

A method in accordance with another aspect of the disclosure includes steps of: by the IMU, obtaining angular velocity data of the wearable electronic device during a unit of time; by the processing unit, calculating a sway angle of the body part with respect to the unit of time based on the angular velocity data measured during the unit of time; by the processing unit, determining whether the sway angle thus calculated exceeds an angle threshold that is associated with the user and that is related to sway of the body part of the user when walking a plurality of steps while maintaining balance; and by the processing unit, when it is determined that the sway angle exceeds the angle threshold, controlling the output unit to output a first signal that indicates imbalance of the user.

According to one aspect of the disclosure, the wearable electronic device for warning a user of imbalance includes a main body, an inertial measurement unit (IMU), a processing unit and an output unit. The main body is configured to be fastened to a body part of the user in a manner that the main body moves synchronously with the body part of the user. The IMU is attached to the main body and is configured to obtain acceleration data and angular velocity data of the main body. The processing unit is attached to the main body and is electrically connected to the IMU. The output unit is attached to the main body, and is electrically connected to and controlled by the processing unit. When the wearable electronic device is operating in a calibration mode, the IMU is configured to obtain the acceleration data during a calibration period, in which the user continuously takes a plurality of steps walking on the ground while maintaining balance, and to send the acceleration data thus obtained to the processing unit. Further, when the wearable electronic device is operating in a calibration mode, the processing unit is configured to obtain an angle threshold based on the acceleration data received from the IMU, wherein the angle threshold is related to sway of the body part of the user. When the wearable electronic device is operating in a monitoring mode, the IMU is configured to obtain the angular velocity data during a unit of time and to send the angular velocity data thus obtained to the processing unit. Further, when the wearable electronic device is operating in a monitoring mode, the processing unit is configured to calculate a sway angle of the body part with respect to the unit of time based on the angular velocity data measured during the unit of time, to determine whether the sway angle thus calculated exceeds the angle threshold, and to control the output unit to output a first signal that indicates imbalance of the user when it is determined that the sway angle exceeds the angle threshold.

BRIEF DESCRIPTION OF THE DRAWINGS

Other features and advantages of the disclosure will become apparent in the following detailed description of the embodiment (s) with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1:
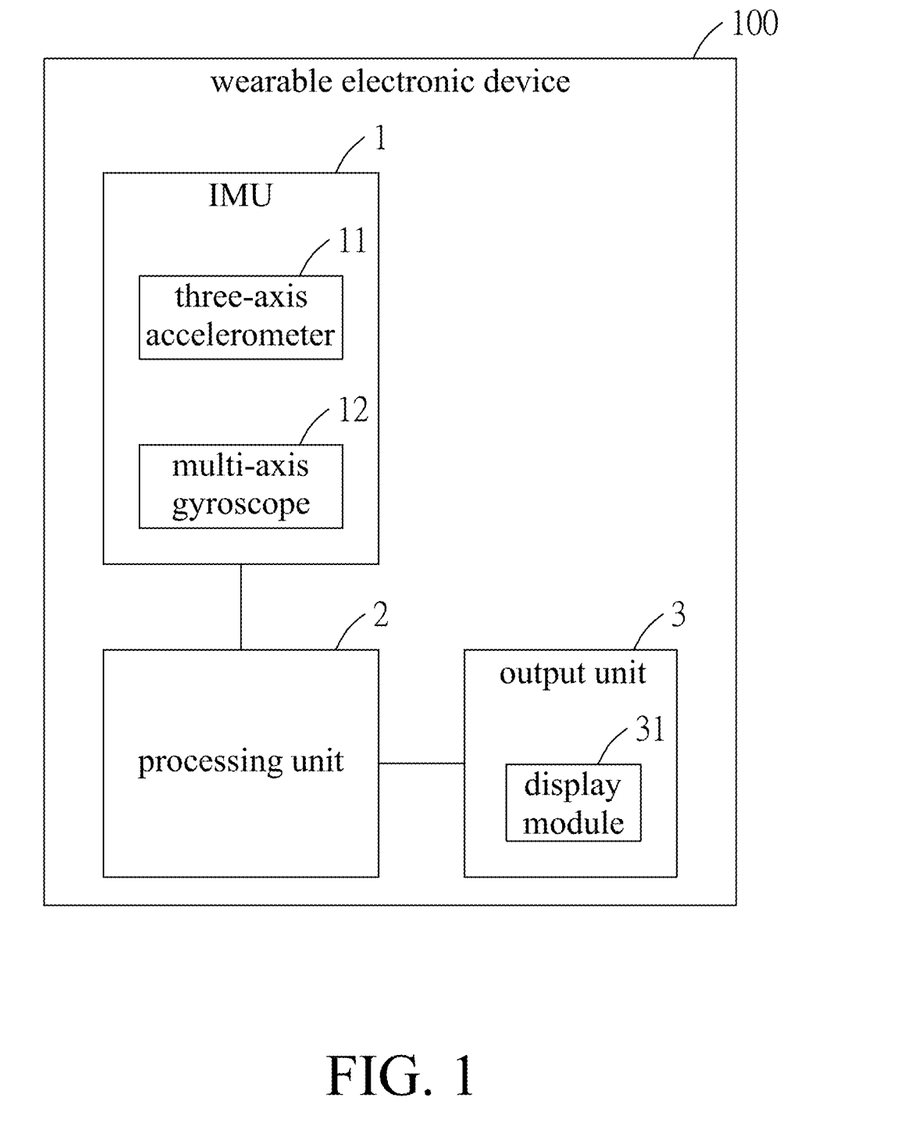
FIG. 1 exemplarily illustrates a block diagram of a wearable electronic device according to an embodiment of the disclosure.

Referring to FIG. 1, a wearable electronic device 100 for warning a user of imbalance is illustrated in accordance with an embodiment of the disclosure. The wearable electronic device 100 includes an inertial measurement unit (IMU) 1, a processing unit 2 electrically connected to the IMU 1, and an output unit electrically connected to and controlled by the processing unit 2. The processing unit 2 may be exemplified by a processor, a central processing unit (CPU), a digital signal processor (DSP), a system on a chip (SoC) or any other device having computation capability.

Figure 2:
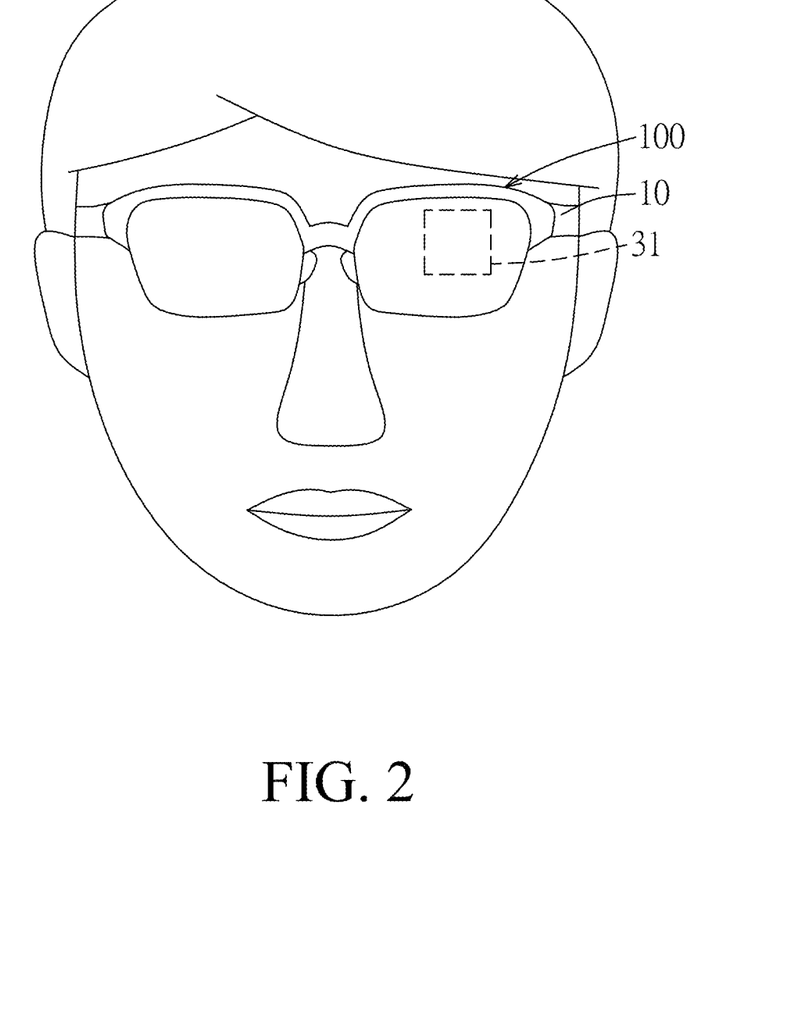
FIG. 2 exemplarily illustrates a schematic diagram of the wearable electronic device implemented as a pair of eyeglasses according to an embodiment of the disclosure.

The wearable electronic device 100 has a main body that is configured to be fastened to a body part of the user in a manner that the main body moves synchronously with the body part of the user, and the IMU 1, the processing unit 2 and the output unit 3 are all mounted to the main body. Referring to FIG. 2, in an embodiment, the wearable electronic device 100 is implemented as a pair of smart glasses, and the pair of smart glasses has an eyeglass frame that is configured to be fastened to the head of the user in order to move synchronously with the head of the user and that serves as the main body 10. However, the disclosure is not limited to eyeglasses; for example, the wearable electronic device 100 may also be implemented as an earphone, a badge or a waistband.

The IMU 1 is configured to obtain acceleration data and angular velocity data of the main body 10. As illustrated in FIG. 1, the IMU 1 includes a three-axis accelerometer 11 and a multi-axis gyroscope 12. The three-axis accelerometer 11 is configured to measure accelerations of the main body 10 in three directions that are perpendicular to each other. The multi-axis gyroscope 12 is configured to measure angular velocities of the main body 10 about at least two axes.

The output unit 3 includes a display module 31, and is configured to output a visual signal in response to instructions from the processing unit 2. In an embodiment in which the wearable electronic device 100 is implemented as a pair of smart glasses, the display module 31 is a transparent display screen incorporated in a lens, but the disclosure is not limited thereto. According to some embodiments, the display module 31 may include at least one lighting element (e.g., light-emitting diode (LED)) for delivering the visual signal. In some embodiments, the output unit 3 may further include a sounding element (e.g., speaker) for delivering an audio signal.

Figure 3:
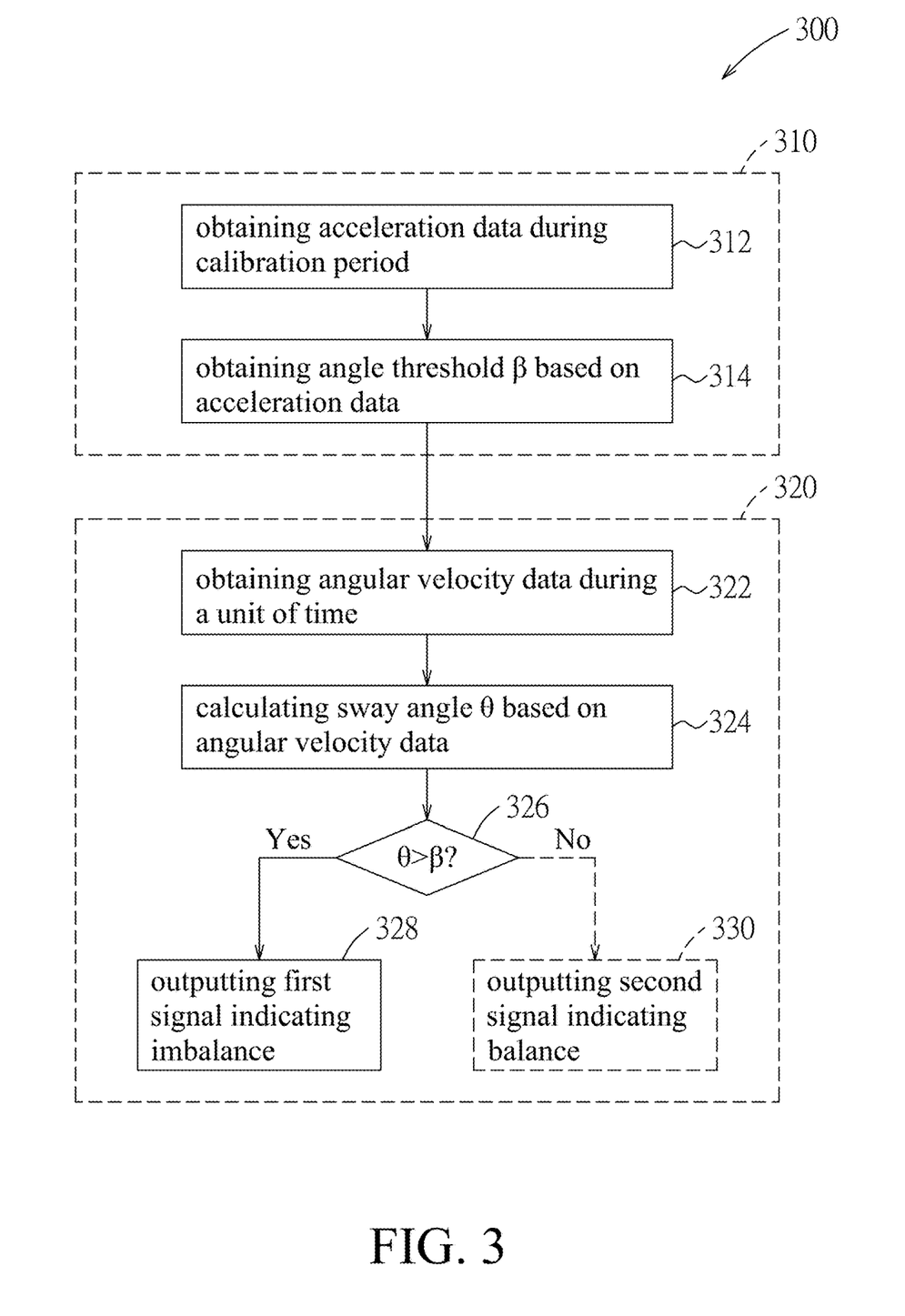
FIG. 3 exemplarily illustrates a flow chart of a method for imbalance warning to be implemented by the wearable electronic device of FIG. 1 according to an embodiment of the disclosure.

The wearable electronic device 100 may operate to implement a method for imbalance warning when a user is wearing the wearable electronic device 100 with the main body 10 being fastened to a body part of the user and moving synchronously with the body part of the user. As illustrated in FIG. 3, an embodiment of the method 300 for imbalance warning includes a calibration procedure 310 in which the wearable electronic device 100 operates in a calibration mode, and a monitoring procedure 320 in which the wearable electronic device 100 operates in a monitoring mode.

The calibration procedure 310 is preparation work for setting the wearable electronic device 100, and includes Steps 312 and 314. In Step 312, the IMU 1 obtains acceleration data related to the wearable electronic device 100 during a calibration period, in which the user takes N number of consecutive steps walking on the ground while maintaining balance, where N is an integer greater than one. Specifically, the IMU 1 obtains the acceleration data that includes first acceleration values of a first acceleration in a first direction (also referred to as X direction hereinafter), second acceleration values of a second acceleration in a second direction (also referred to as Y direction hereinafter) that is perpendicular to the X direction, and third acceleration values of a third acceleration in a third direction (also referred to as Z direction hereinafter) that is perpendicular to the X and Y directions by means of the three-axis accelerometer 11. In an embodiment, the X direction is a front-back direction of the wearable electronic device 100 and relates to an anteroposterior axis of the user, and the Y direction is a lateral direction (left-right) perpendicular to the X direction, but the disclosure is not limited thereto. According to some embodiments, the X and Y directions may define a surface parallel to the ground on which the user is walking. The IMU 1 sends the acceleration data thus obtained to the processing unit 2.

Figure 4:
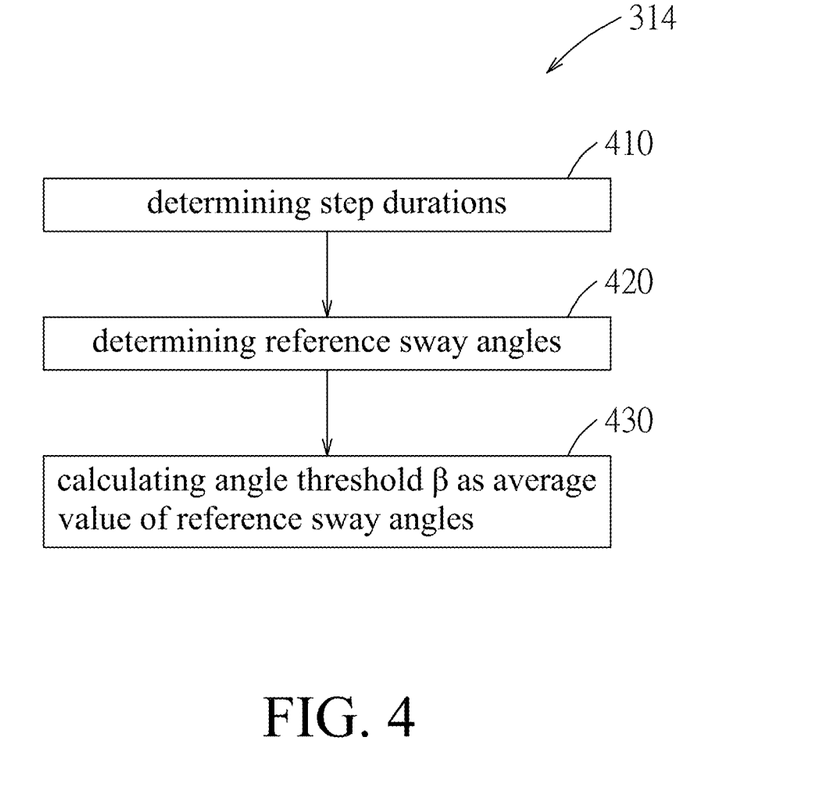
FIG. 4 exemplarily illustrates a flow chart of sub-steps of Step 314 of FIG. 3 according to an embodiment of the disclosure.

In Step 314, the processing unit 2 obtains an angle threshold $\beta$ based on the acceleration data received from the IMU 1. The angle threshold $\beta$ is associated with the user and is related to sway of the body part of the user. As illustrated in FIG. 4, Step 314 includes Sub-steps 410-430.

Figure 5:
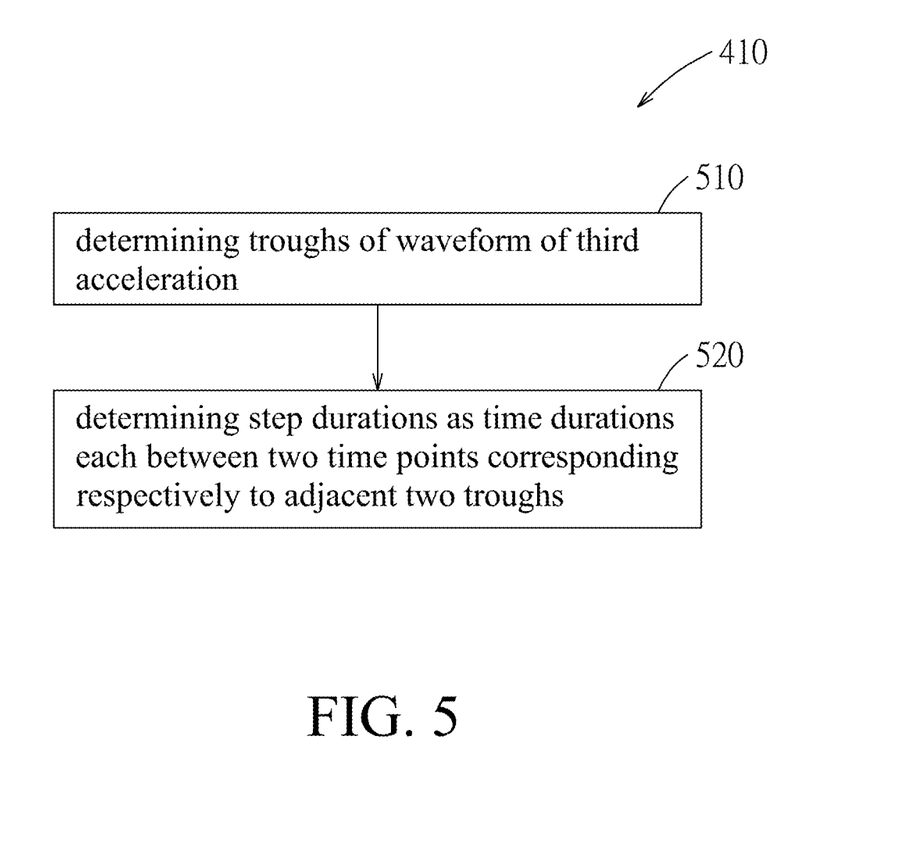
FIG. 5 exemplarily illustrates a flow chart of sub-steps of Sub-step 410 of FIG. 4 according to an embodiment of the disclosure.

In Sub-step 410, the processing unit 2 determines N number of step durations that correspond respectively to the N number of steps. Sub-step 410 further includes two Sub-steps 510 and 520 that are illustrated in FIG. 5. In Sub-step 510, the processing unit 2 determines N+1 number of troughs of a waveform of the third acceleration that is composed of the third acceleration values which are measured during the calibration period. In Sub-step 520, the processing unit 2 determines the N number of step durations respectively as N number of time durations each between two time points corresponding respectively to adjacent two of the N+1 number of troughs.

Figure 6:
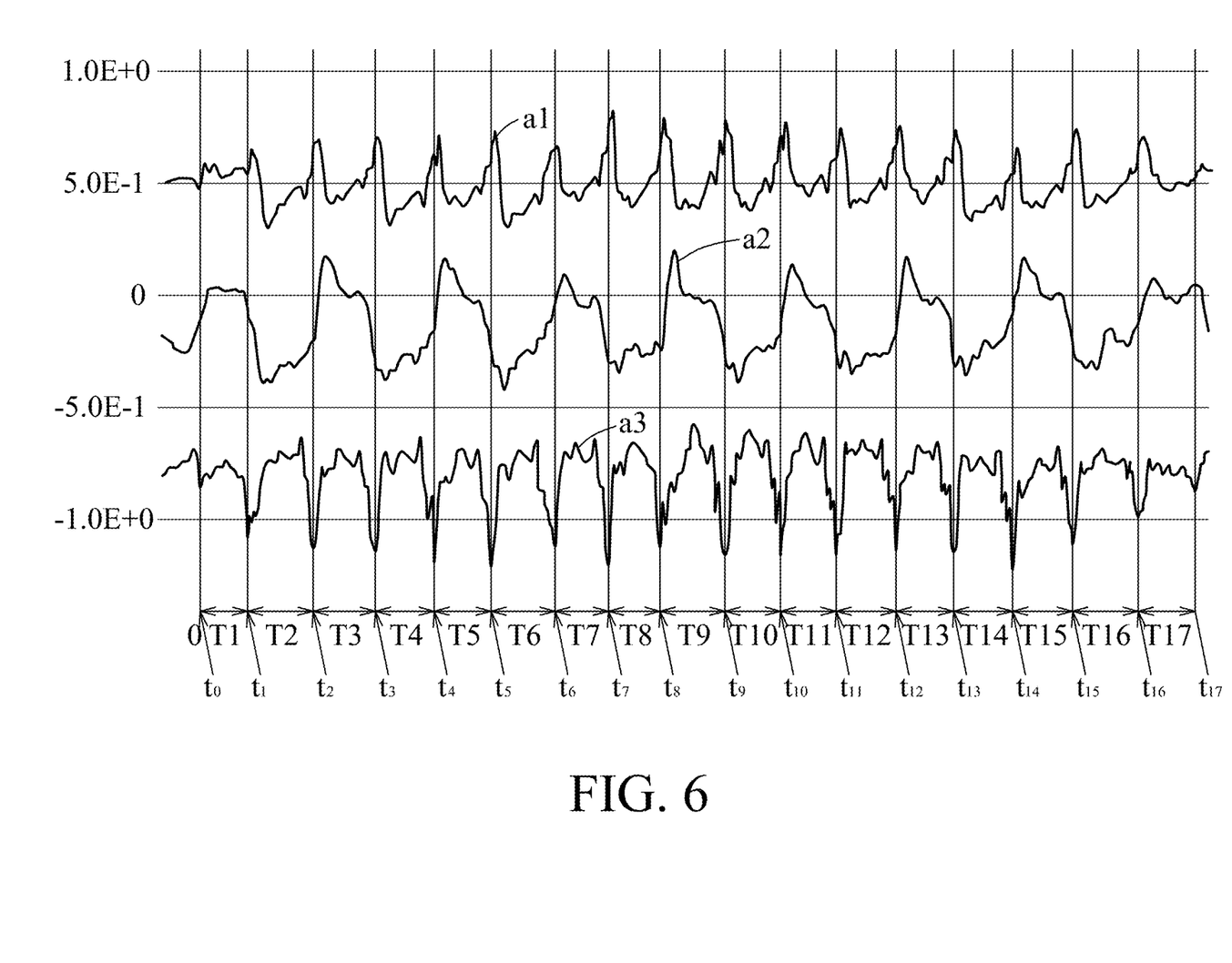
FIG. 6 illustrates exemplary waveforms of accelerations in three different directions according to an embodiment of the disclosure.

FIG. 6 exemplarily illustrates experimental results of the first through third accelerations measured by the IMU 1 during a calibration period, in which the user walks seventeen (17) steps (i.e., N=17). The exemplary waveform a1 is composed of the first acceleration values thus measured, the exemplary waveform a2 is composed of the second acceleration values thus measured, and the exemplary waveform a3 is composed of the third acceleration values thus measured. In the example of FIG. 6, the processing unit 2 may first, in Sub-step 510, determine eighteen (18) troughs of the waveform a3 respectively at time points $t_0$-$t_{17}$, and then, in Sub-step 520, determine a first step duration T1 as the time duration between the time points $t_0$ and $t_1$, a second step duration T2 as the time duration between the time points $t_1$ and $t_2$, and so on, until the last, seventeenth step duration T17 between the time points $t_{16}$ and $t_{17}$ is determined.

Figure 7:
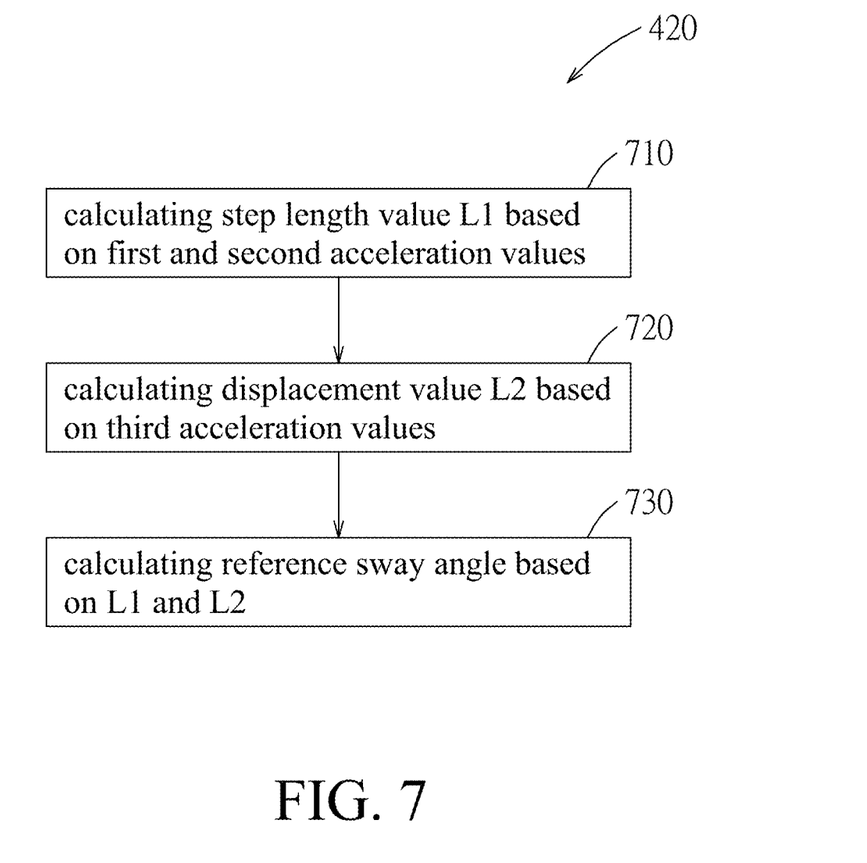
FIG. 7 exemplarily illustrates a flow chart of sub-steps of Sub-step 420 of FIG. 4 according to an embodiment of the disclosure.

Returning to FIG. 4, in Sub-step 420, the processing unit 2 determines N number of reference sway angles $\beta_r$ respectively for the N number of step durations. Sub-step 420 further includes Sub-steps 710-730 that are illustrated in FIG. 7 and that are performed for each of the N number of step durations.

In Sub-step 710, the processing unit 2 calculates a step length value L1 for the step duration based on the first and second acceleration values measured during the step duration. The step length value L1 relates to a distance the user walked during the step duration (i.e., a stride length). According to an embodiment, the step length value L1 may be calculated by performing double integration on the first acceleration over time to obtain an X-direction distance $\alpha_x$, performing double integration on the second acceleration over time to obtain a Y-direction distance $\alpha_y$, and then calculating the step length value L1 as $$\sqrt{\alpha_x^2 + \alpha_y^2}.$$

It should be appreciated that integration on the acceleration measured during the step duration means integration on a segment of the waveform of the acceleration between the time points corresponding to the step duration. For example, continuing with the example shown in FIG. 6, a first step length value $L1_1$ for the first step duration T1 may be obtained by performing double integration on a segment of the waveform a1 of the first acceleration over time between time points $t_0$ and $t_1$ to obtain a first X-direction distance $\alpha_{x1}$, performing double integration on a segment of the waveform a2 of the second acceleration over time between time points $t_0$ and $t_1$ to obtain a first Y-direction distance $\alpha_{y1}$, and then calculating the first step length value $L1_1$ as $$\sqrt{\alpha_{x1}^2 + \alpha_{y1}^2}.$$

In Sub-step 720, the processing unit 2 calculates a displacement value L2 for the step duration based on the third acceleration values measured during the step duration. The displacement value L2 relates to displacement of the body part in the third direction. According to an embodiment, the displacement value L2 may be calculated by performing double integration on the third acceleration over time. For example, continuing with the example shown in FIG. 6, a first displacement value $L2_1$ for the first step duration T1 may be obtained by performing double integration on a segment of the waveform a3 of the third acceleration over time between time points $t_0$ and $t_1$.

In Sub-step 730, the processing unit 2 calculates a reference sway angle $\beta_r$ for the step duration as $\cot^{-1}(L1/L2)$. For example, continuing with the example shown in FIG. 6, a first reference sway angle $\beta_{r1}$ for the first step duration T1 may be calculated as $\cot^{-1}(L1_1/L2_1)$.

Figure 8:
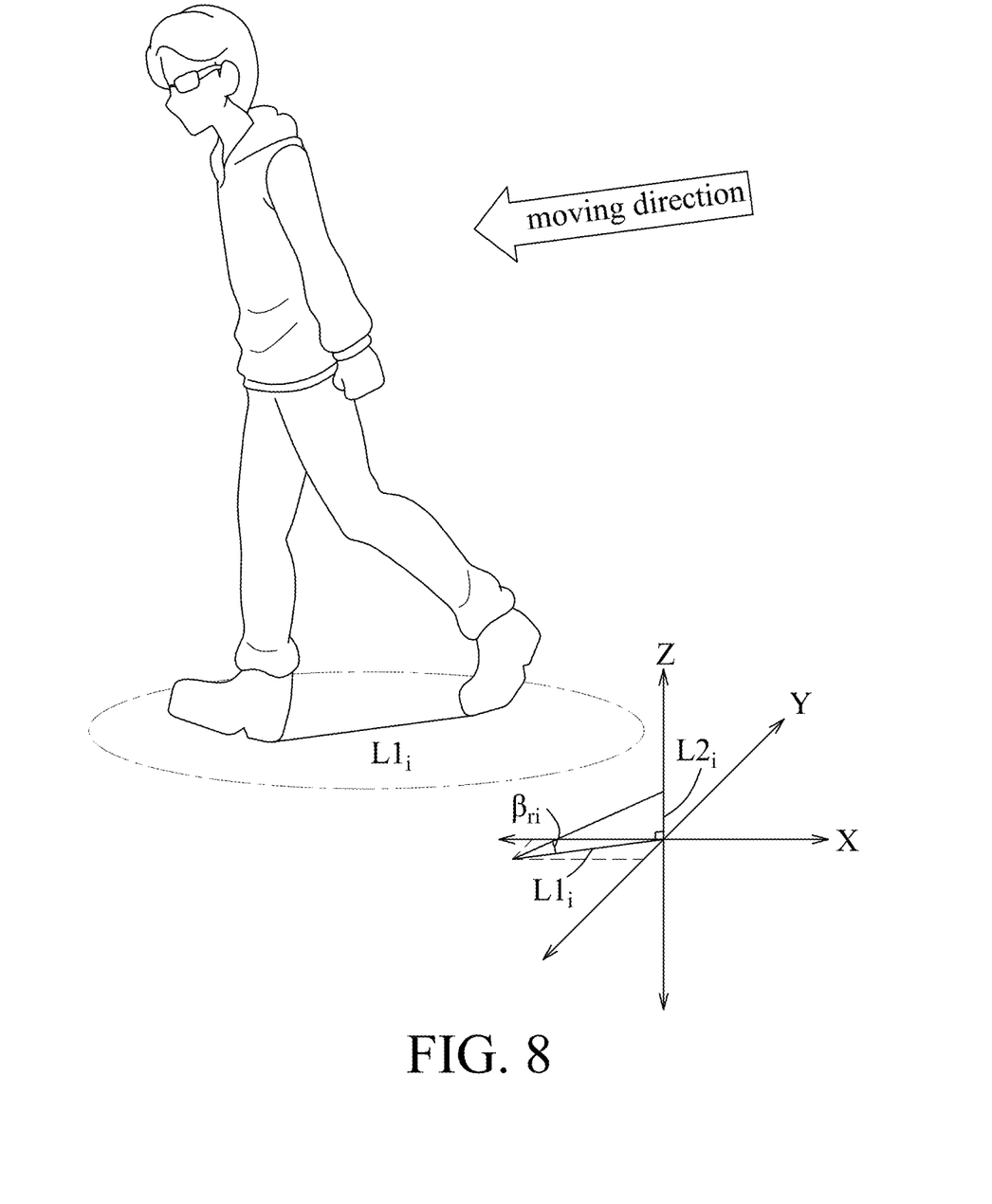
FIG. 8 exemplarily illustrates a schematic diagram showing an exemplary reference sway angle according to an embodiment of the disclosure.

After Sub-steps 710-730 of Sub-step 420 are repeated for each of the N number of step durations, N number of reference sway angles $\beta_{ri}$ (i=1, 2, ... N) can be obtained. A schematic diagram showing an exemplary step length value $L1_i$, an exemplary displacement value $L2_i$ and an exemplary reference sway angle $\beta_{ri}$ for an i-th step duration Ti with reference to the X, Y, Z directions can be seen in FIG. 8.

In Sub-step 430, the processing unit 2 calculates the angle threshold $\beta$ as an average value of the N number of reference sway angles $\beta_{ri}$ calculated respectively for the N number of step durations.

Referring back to FIG. 3, the monitoring procedure 320 for monitoring postural balance of the user includes Steps 322-328 that are performed every unit of time. According to an embodiment, the length of the unit of time may equal the sampling period of the multi-axis gyroscope 12, but the disclosure is not limited thereto.

In Step 322, the IMU 1 obtains, by means of the multi-axis gyroscope 12, angular velocity data of the wearable electronic device 100 during a unit of time, and sends the angular velocity data thus obtained to the processing unit 2. Specifically, the angular velocity data includes a first angular velocity $\omega_{roll}$ about a first axis extending in the X direction and a second angular velocity $\omega_{pitch}$ about a second axis extending in the Y direction that are measured by the multi-axis gyroscope 12 during the unit of time.

In Step 324, the processing unit 2 calculates a sway angle $\theta$ of the body part with respect to the unit of time based on the angular velocity data received from the IMU 1. The sway angle $\theta$ relates to sway with reference to the anteroposterior axis of the user during the unit of time. Specifically, the processing unit 2 may first combine the first angular velocity $\omega_{roll}$ and the second angular velocity $\omega_{pitch}$ to obtain a resultant angular velocity $\omega_{rp}$ using an equation of $$\omega_{rp} = \sqrt{\omega_{roll}^2 + \omega_{pitch}^2},$$

and then calculate the sway angle $\theta$ by integrating the resultant angular velocity $\omega_{rp}$ over the unit of time.

Figure 9:
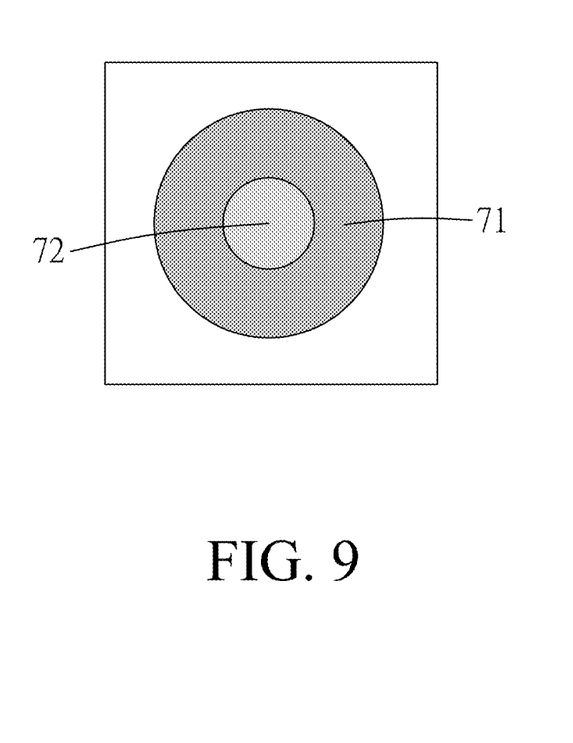
FIG. 9 exemplarily illustrates an implementation of a visual signal indicating imbalance/balance of the user according to an embodiment of the disclosure.

In Step 326, the processing unit 2 determines whether the sway angle $\theta$ thus calculated exceeds the angle threshold $\beta$ previously obtained in Step 314 of the calibration procedure 310. When it is determined that the sway angle $\theta$ exceeds the angle threshold the process goes to Step 328, in which the processing unit 2 controls the output unit 3 to output a first signal that indicates imbalance of the user. According to some embodiments, the first signal outputted by the output unit 3 may include at least one of a visual signal or an audio signal (namely, one or both of the visual signal and the audio signal). For example, in some embodiments, the output unit 3 outputs the first signal by displaying a glowing or flashing pattern (e.g., a ring 71 glowing in red shown in FIG. 9) on the display module 31. In some other embodiments, the output unit 3 outputs the first signal by making a beeping sound. The first signal may warn the user of a tendency toward an imbalance crisis (such as falling-down), so that the user may react in time, e.g., to adjust his/her posture or to stop walking, to avoid the imbalance crisis.

According to some embodiments, the monitoring procedure 320 may optionally include Step 330 that is performed when it is determined in Step 326 that the sway angle $\theta$ does not exceed the angle threshold $\beta$. In Step 330, the processing unit 2 controls the output unit 3 to output a second signal that indicates balance of the user. According to some embodiments, the second signal outputted by the output unit 3 may include at least one of a visual signal. For example, in some embodiments, the output unit 3 outputs the second signal by displaying a glowing pattern (e.g., a round disc 72 glowing in green shown in FIG. 9) on the display module 31.

In summary, the wearable electronic device 100 and the method 300 for imbalance warning disclosed herein first in the calibration procedure 310 determine and set an angle threshold β that is customized to the user who is wearing the wearable electronic device 100 and that fully reflects the balance control ability of the user, and then in the monitoring procedure 320 monitor balance state of the user based on the customized angle threshold β, such that the judgment criteria for outputting an imbalance warning signal (i.e., the first signal mentioned above) is not too loose to effectively protect the user, and is not too strict that the user may be troubled by over-frequent warnings. In addition, the customized angle threshold β as disclosed may be utilized as an important parameter in designing or adjusting other assistive devices for balance, so as to improve suitability of these assistive devices to the user.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for imbalance warning to be implemented by a wearable electronic device positioned on a body part of a user, the wearable electronic device including an inertial measurement unit (IMU), an output unit and a processing unit electrically connected to the IMU and the output unit, the IMU including a three-axis accelerometer, the method comprising steps of:

by the IMU, obtaining acceleration data related to the wearable electronic device during a calibration period, in which the user continuously takes a plurality of steps walking on the ground while maintaining balance, wherein the acceleration data include first acceleration values in a first direction, second acceleration values in a second direction that is perpendicular to the first direction, and third acceleration values in a third direction that is perpendicular to the first and second directions, the first direction relating to an anteroposterior axis of the user;

by the processing unit, obtaining an angle threshold that is associated with the user and that is related to sway of the body part of the user based on the acceleration data thus obtained through sub-steps of:

determining a plurality of step durations that correspond respectively to the steps;

for each of the step durations,
calculating a step length value of the step based on the first and second acceleration values that are measured during the step duration,
calculating a displacement value based on the third acceleration values that are measured during the step duration, the displacement value relating to displacement of the body part in the third direction, and
calculating a reference sway angle as $\cot^{-1}(L1/L2)$, where L1 represents the step length value and L2 represents the displacement value; and calculating the angle threshold as an average value of the reference sway angles calculated respectively for the step durations;

by the IMU, obtaining angular velocity data of the wearable electronic device during a unit of time;

by the processing unit, calculating a sway angle of the body part with respect to the unit of time based on the angular velocity data measured during the unit of time;

by the processing unit, determining whether the sway angle thus calculated exceeds the angle threshold; and by the processing unit, when it is determined that the sway angle exceeds the angle threshold, controlling the output unit to output a first signal that indicates imbalance of the user.

2. The method of claim 1, further comprising a step of:
by the processing unit, when it is determined that the sway angle does not exceed the angle threshold, controlling the output unit to output a second signal that indicates balance of the user.

3. The method of claim 1, wherein the sub-step of determining a plurality of step durations includes sub-steps of:

determining a plurality of troughs of a waveform that is composed of the third acceleration values which are measured during the calibration period; and determining the step durations respectively as plural time durations each between two time points corresponding respectively to adjacent two of the troughs.

4. The method of claim 1, the IMU further including a multi-axis gyroscope that has a sampling period equal to a length of the unit of time, wherein:

the step of obtaining angular velocity data includes measuring, during the unit of time, a first angular velocity about a first axis extending in the first direction, and a second angular velocity about a second axis extending in the second direction; and the step of calculating a sway angle is to calculate the sway angle that relates to sway with reference to the anteroposterior axis of the user during the unit of time.

5. The method of claim 1, wherein the step of controlling the output unit to output a first signal is to control the output unit to output the first signal that includes at least one of a visual signal or an audio signal.

6. A method for imbalance warning to be implemented by a wearable electronic device positioned on a body part of a user, the wearable electronic device including an inertial measurement unit (IMU), an output unit and a processing unit electrically connected to the IMU and the output unit, the IMU including a three-axis accelerometer, the method comprising steps of:

by the IMU, obtaining acceleration data related to the wearable electronic device during a calibration period, in which the user continuously takes a plurality of steps walking on the ground, wherein the acceleration data include first acceleration values in a first direction, second acceleration values in a second direction that is perpendicular to the first direction, and third acceleration values in a third direction that is perpendicular to the first and second directions, the first direction relating to an anteroposterior axis of the user;

by the processing unit, obtaining an angle threshold based on the acceleration data thus obtained through substeps of:
- determining a plurality of troughs of a waveform that is composed of the third acceleration values that are measured during the calibration period;
- determining plural step durations respectively as plural time durations each between two time points corresponding respectively to adjacent two of the troughs;
- for each of the step durations,
  - calculating a step length value of the step based on the first and second acceleration values that are measured during the step duration,
  - calculating a displacement value based on the third acceleration values that are measured during the step duration, the displacement value relating to displacement of the body part in the third direction, and
  - calculating a reference sway angle as $\cot^{-1}(L1/L2)$, where L1 represents the step length value and L2 represents the displacement value; and
- calculating the angle threshold as an average value of the reference sway angles calculated respectively for the step durations;

by the IMU, obtaining angular velocity data of the wearable electronic device during a unit of time;

by the processing unit, calculating a sway angle of the body part with respect to the unit of time based on the angular velocity data measured during the unit of time;

by the processing unit, determining whether the sway angle thus calculated exceeds an angle threshold that is associated with the user and that is related to sway of the body part of the user when walking a plurality of steps while maintaining balance; and by the processing unit, when it is determined that the sway angle exceeds the angle threshold, controlling the output unit to output a first signal that indicates imbalance of the user.

7. The method of claim 6, the IMU further including a multi-axis gyroscope that has a sampling period equal to a length of the unit of time, wherein:
- the step of obtaining angular velocity data includes measuring, during the unit of time, a first angular velocity about a first axis extending in the first direction, and a second angular velocity about a second axis extending in the second direction; and
- the step of calculating a sway angle is to calculate the sway angle that relates to sway with reference to the anteroposterior axis of the user during the unit of time.

8. The method of claim 7, wherein the step of calculating a sway angle includes:
- combining the first angular velocity and the second angular velocity to obtain a resultant angular velocity; and
- calculating the sway angle by integrating the resultant angular velocity over the unit of time.

9. A wearable electronic device for warning a user of imbalance, comprising:
- a main body configured to be fastened to a body part of the user in a manner that said main body moves synchronously with the body part of the user;
- an inertial measurement unit (IMU) attached to said main body and configured to obtain acceleration data and angular velocity data of said main body, the IMU including:
  - a three-axis accelerometer configured to obtain the acceleration data that include first acceleration values in a first direction, second acceleration values in a second direction that is perpendicular to the first direction, and third acceleration values in a third direction that is perpendicular to the first and second directions, the first direction relating to an anteroposterior axis of the user; and
  - a multi-axis gyroscope configured to obtain the angular velocity data that include a first angular velocity about a first axis extending in the first direction, and a second angular velocity about a second axis extending in the second direction;
- a processing unit attached to said main body and electrically connected to said IMU; and
- an output unit attached to said main body, and electrically connected to and controlled by said processing unit, wherein, when said wearable electronic device is operating in a calibration mode, said IMU is configured to obtain the acceleration data during a calibration period, in which the user continuously takes a plurality of steps walking on the ground while maintaining balance, and to send the acceleration data thus obtained to said processing unit, and said processing unit is configured to obtain an angle threshold that is related to sway of the body part of the user based on the acceleration data received from said IMU by
- determining a plurality of step durations that correspond respectively to the steps;
- for each of the step durations,
  - calculating a step length value of the step based on the first and second acceleration values that are measured during the step duration,
  - calculating a displacement value based on the third acceleration values that are measured during the step duration, the displacement value relating to displacement of the body part in the third direction, and
  - calculating a reference sway angle as $\cot^{-1}(L1/L2)$, where L1 represents the step length value and L2 represents the displacement value; and
- calculating the angle threshold as an average value of the reference sway angles calculated respectively for the step durations, wherein, when said wearable electronic device is operating in a monitoring mode, said IMU is configured to obtain the angular velocity data during a unit of time and to send the angular velocity data thus obtained to said processing unit, and said processing unit is configured to calculate a sway angle of the body part with respect to the unit of time based on the angular velocity data measured during the unit of time, to determine whether the sway angle thus calculated exceeds the angle threshold, and to control said output unit to output a first signal that indicates imbalance of the user when it is determined that the sway angle exceeds the angle threshold.

10. The wearable electronic device of claim 9, wherein said processing unit is further configured to, when said wearable electronic device is operating in the monitoring mode, control said output unit to output a second signal that indicates balance of the user when it is determined that the sway angle does not exceed the angle threshold.

11. The wearable electronic device of claim 9, wherein said processing unit is configured to
- determine a plurality of troughs of a waveform that is composed of the third acceleration values that are measured during the calibration period; and
- determine the step durations respectively as plural time durations each between two time points corresponding respectively to adjacent two of the troughs.

12. The wearable electronic device of claim 9, wherein said multi-axis gyroscope has a sampling period equal to a length of the unit of time, and the sway angle of the body part calculated by said processing unit relates to sway with reference to the anteroposterior axis of the user.

13. The wearable electronic device of claim 9, wherein the first signal outputted by said output unit includes at least one of a visual signal or an audio signal.

* * * * *